(12) United States Patent
Rice et al.

(10) Patent No.: US 9,290,802 B2
(45) Date of Patent: *Mar. 22, 2016

(54) DETECTION AND QUANTIFICATION OF NUCLEIC ACID TO ASSESS MICROBIAL BIOMASS IN PAPER DEFECTS AND MACHINE FELTS

(71) Applicant: NALCO COMPANY, Naperville, IL (US)

(72) Inventors: Laura E. Rice, St. Charles, IL (US); Liliya Lund, Warrenville, IL (US)

(73) Assignee: NALCO COMPANY, Naperville, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/138,526

(22) Filed: Dec. 23, 2013

(65) Prior Publication Data
US 2014/0141443 A1 May 22, 2014

Related U.S. Application Data

(63) Continuation-in-part of application No. 13/374,949, filed on Jan. 24, 2012, now Pat. No. 8,613,837.

(51) Int. Cl.
*C12P 19/24* (2006.01)
*C12Q 1/68* (2006.01)
*D21H 17/00* (2006.01)
*D21H 21/04* (2006.01)

(52) U.S. Cl.
CPC ............... *C12Q 1/686* (2013.01); *C12Q 1/689* (2013.01); *D21H 17/00* (2013.01); *D21H 21/04* (2013.01)

(58) Field of Classification Search
USPC ............ 162/158, 161, 198, 49, 263; 435/6.1, 435/6.11, 6.12; 536/23.1, 24.3, 24.32, 536/24.33
See application file for complete search history.

(56) References Cited

U.S. PATENT DOCUMENTS

| | | | |
|---|---|---|---|
| 3,817,828 A * | 6/1974 | Bendiner | 162/161 |
| 5,928,875 A * | 7/1999 | Breen et al. | 435/6.15 |
| 7,949,432 B2 | 5/2011 | Rice | |
| 8,613,837 B2 * | 12/2013 | Rice et al. | 162/198 |
| 2004/0014122 A1 | 1/2004 | Breen et al. | |
| 2009/0294082 A1 * | 12/2009 | Kolari | 162/158 |
| 2010/0227332 A1 * | 9/2010 | Iizumi et al. | 435/6 |
| 2011/0067832 A1 * | 3/2011 | Xia et al. | 162/161 |

FOREIGN PATENT DOCUMENTS

| | | | |
|---|---|---|---|
| JP | 3788999 B2 | | 6/2006 |
| JP | 2006-217869 A | * | 8/2006 |
| JP | 2006217869 A | | 8/2006 |
| WO | 2004042082 A1 | | 5/2004 |
| WO | WO 2004/042082 A1 | * | 5/2004 |

* cited by examiner

Primary Examiner — Dennis Cordray
(74) Attorney, Agent, or Firm — Fredrikson & Byron, P.A.

(57) ABSTRACT

The invention is directed towards methods and compositions for identifying the specific microorganisms present in a particular potion of a papermaking processes. The method involves obtaining a sample from the process which is such that little or no live examples of the microorganism remain. However because DNA from the organisms is still present, an analysis which identifies portions of DNA specific to the particular organism will correctly identify the microorganism present. This allows for analysis of infestations present on felts or paper sheets which typically no longer have many live microorganisms on them when samples are taken for analysis.

14 Claims, 4 Drawing Sheets

DETECTION AND QUANTIFICATION OF NUCLEIC ACID TO ASSESS MICROBIAL BIOMASS IN PAPER DEFECTS AND MACHINE FELTS

CROSS-REFERENCE TO RELATED APPLICATIONS

This Application is a Continuation-In-Part of co-pending U.S. patent application Ser. No. 13/374,949. filed on Jan. 24, 2012.

STATEMENT REGARDING FEDERALLY SPONSORED RESEARCH OR DEVELOPMENT

Not Applicable.

BACKGROUND OF THE INVENTION

The present invention relates generally to compositions of matter, apparatuses and methods useful in detecting and identifying microorganisms causing or present in machine felts and on paper defects.

As described for example in U.S. Pat. Nos. 7,306,702and 5,928,875, paper is produced in a continuous manner from a fibrous suspension (pulp furnish) generally made of water and cellulose fibers. A typical paper manufacturing process consists of 3 stages: forming, pressing, and drying. In the forming stage, dilute pulp furnish is directed on a wire or between 2wires. The majority of the water is drained from the pulp furnish, through the wire, creating a wet paper web. In the pressing stage the paper web comes in contact with one or generally more porous Machine Felts that are used to extract much of the remaining water from the web. Often the pickup felt is the first felt that the wet paper web contacts which is used to remove the paper web from the wire, via a suction pickup roll positioned behind the felt, and then to transport the paper web to the rest of the press section. The paper web then generally passes through one or more presses each consisting of rotating press rolls and/or stationary elements such as press shoes that are positioned in close proximity to each other forming, what is commonly referred to as, a press nip. In each nip the paper web comes in contact with either one or two Machine Felts where water is forced from the paper web and into the press felt via pressure and/or vacuum. In single-felted press nips the paper web is in contact with the press roll on one side and the felt on the other. In double-felted press nips, the paper web passes between the two felts.

After the press section, the paper web is dried to remove the remaining water, usually by weaving through a series of steam heated dryer cans.

Machine felts often consist of wool or nylon base fabric generally made of from 1 to 4individual layers of filaments arranged in a weave pattern. An extruded polymeric membrane or mesh can also be included as one or more of the base fabric layers. Batt fibers, of smaller diameter than the base fabric filaments, are needled into the base on both sides giving the felt a thick, blanket-like appearance. Machine Felts are designed to quickly take in water from the paper web in the nip and hold the water so that it does not re-absorb back into the sheet as the paper and felt exit the press nip. Machine Felts are normally a belt passing through an endless loop that circulates continuously between sheet contact stages and return stages. Water pulled into the felt from the paper web at the nip is generally removed from the felt by vacuum during the felt return stage at, what is frequently referred to as, the uhle box.

Papermaking systems utilize several raw materials that introduce microorganisms into the machine system. This includes virgin wood fiber, recycled fiber, freshwater, starch, dyes, and other chemical additives. Microorganisms proliferate in many or all of the warm, nutrient rich environments present within papermaking systems and diverse microbial communities result. Inadequate control of microbial growth allows for the formation of surface deposits that slough, leading to filter or nozzle plugging and defects (e.g. spots or holes) or breaks in the sheet. Microorganisms can also proliferate in the felts and machine fabrics, negatively impacting water removal and machine or operational efficiency. Microbial growth in papermaking systems can be quite harmful and costly. The growth of microorganisms on equipment surfaces can lead to the formation of deposits that slough and contribute to sheet defects and holes. Contaminated shower water treatments or process water can lead to the growth of microbes on felts which commonly result in the formation of plugs on the felts. These plugs in turn cause a number of problems most notably the impairment of water removal from paper web. As a result microbial growth can result in an excessive and costly need for multiple boil-outs and cleanings of felts or other papermaking equipment. These problems can be compounded when an incorrect determination of which microorganisms occurs because this can result in a treatment which further degrades the quality of the paper, further impacts process equipment, and/or may not even control the underlying microbial infestation. Moreover incorrectly distinguishing between biologically caused problems and mechanical or chemical caused problems can further result in inadequate, wasteful, and possibly counter-productive efforts.

A number of prior art methods are known for identifying which microorganisms are present in a papermaking system. These methods however are particularly deficient when applied to paper sheets or felts. Some of the prior art methods such as U.S. Pat. Nos. 8,012,758, 7,981,679, and 7,949, 432detect various effects in the fluids of the papermaking system produced by living microbiological organisms. Other methods such as U.S. Pat. No. 5,281,537rely on obtaining a sample of living microorganism contaminant and growing more of it so as to perform various analyses. In the context of paper sheets and felts however these methods are particularly inadequate as by the time samples of the felt or paper are taken they no longer contain sufficient (or any) live organisms to culture or any of the chemical products that they produce. Also items of the papermaking system (such as paper sheets and felts) that are downstream from the heating or drying sections will have had all the defect causing microorganisms killed off after they have already caused the defects. Alternative methods that do not rely on the presence of live organisms also tend to be deficient because they often produce false positives. For example ninhydrin (which is used to detect primary or secondary amines) and IR spectroscopy often produce false positives or negatives because they detect materials that may have non-biological origins (such as chemical additives or contamination).

Thus it is clear that there is clear utility in novel methods and compositions for the proper identification of microorganisms present on machine felts and paper sheets. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37. CFR § 1.56(a) exists.

BRIEF SUMMARY OF THE INVENTION

At least one embodiment of the invention is directed towards a method of identifying a microorganism infestation in a papermaking process. The method comprises the steps of: 1) noting a defect on an item associated with a papermaking process, 2) conducting at least one DNA Analysis on at least one sample taken from the item, the DNA Analysis may include but is not limited to qPCR, PCR, digital PCR, ion semiconductor sequencing, pyrosequencing, sequencing by synthesis, sequencing by litigation, chain terminating sequencing, and any combination thereof. 3) if a positive result is indicated, determining if a measured concentration of organisms exceeds a pre-determined threshold, 4) if the measured concentration exceeds the threshold at least one additional DNA analysis is done to determine specific organisms that are present in the sample, 5) if the measured concentration of each organism detected exceeds a pre-determined threshold then that defect is at least in part due to an infestation of that organism The item may be a felt. The defect may be one or more plugs in the felt. The item may be a paper sheet produced by the papermaking process and the defect may be one or more holes, discoloration, streaks, spots, translucent spots, and any combination thereof on the paper sheet. The method may further comprise the step of recording the identified organism into a format which can be stored and/or transmitted. The method may further comprise the step of conducting a biocidal program associated with remedying the identified organism. The DNA analysis may be a qPCR analysis. The threshold of the DNA analysis may be $10^4$. cells per ml or $10^4$. cells per gram. The item may be so desiccated that there are no living organisms on the item that may have caused the defect.

The conditions of the item may differ so much from the fluids the item encounters during the papermaking process that the organisms which inhabit the items differ from those in the fluids and determining the inhabitants of the fluids will produce an incorrect identification of the organisms on the item causing the defect. The method may further comprise the step of applying sufficient kinds of primers to samples of the item such that the presence of any organisms above the threshold can be determined. The method may further comprise the step of identifying the defect as being non-biologically based if the DNA analysis does not indicate that any organisms exceed the threshold. The method may further comprise the step of applying a remedy for non-biological chemical contamination to the papermaking process. The DNA analysis may determine the quantity of organisms infesting the sample. The item may have passed through a heat or dryer section of the papermaking process before the defect is noted and therefore the organisms which caused the defect may have been killed.

BRIEF DESCRIPTION OF THE DRAWINGS

A detailed description of the invention is hereafter described with specific reference being made to the drawings in which:

FIG. 1 contains three graphs illustrating the results of samples the invention was applied to.

FIG. 2 illustrates a graph of the total bacterial load of samples the invention was applied to.

FIG. 3 is a graph of the total bacterial load of samples the invention was applied to.

DETAILED DESCRIPTION OF THE INVENTION

Figure 1:
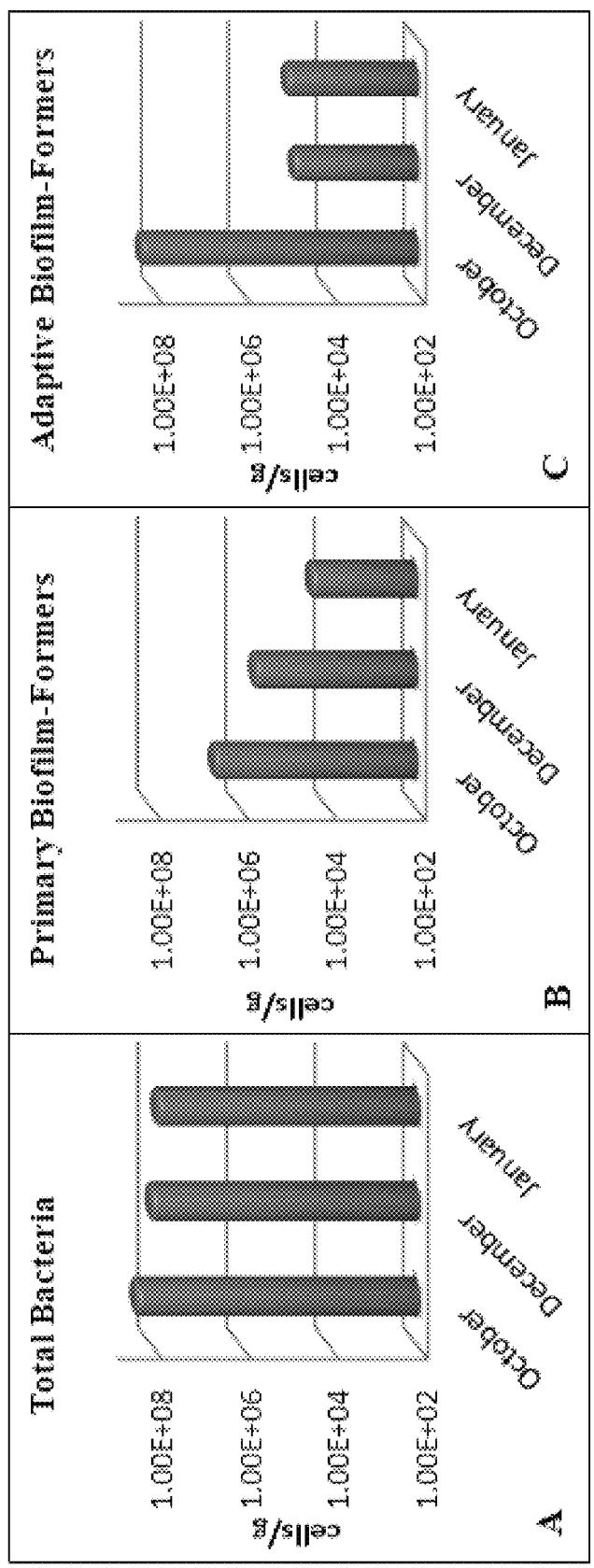

The following definitions are provided to determine how terms used in this application, and in particular how the claims, are to be construed. The organization of the definitions is for convenience only and is not intended to limit any of the definitions to any particular category.

"DNA Based Analysis" means an method of analyzing DNA, including but not limited to qPCR, PCR, digital PCR, ion semiconductor sequencing, pyrosequencing, sequencing by synthesis, sequencing by litigation, chain terminating sequencing, and any combination thereof.

"Ion Torrent Semiconductor Sequencing" means a method of DNA sequencing based on the detection of hydrogen ions that are released during the polymerization of DNA. This is a method of "sequencing by synthesis", during which a complementary strand is built based on the sequence of a template strand, a representative example of this is described at the website: http://www.lifetechnologies.com/us/en/home/life-science/sequencing/next-generation-sequencing/ion-torrent-next-generation-sequencing-technology.html (as accessed on Dec. 23, 2013).

"Pyrosequencing" means a method of DNA sequencing (determining the order of nucleotides in DNA) based on the "sequencing bysynthesis" principle. It differs from Sanger sequencing, in that it relies on the detection of pyrophosphate release on nucleotide incorporation, rather than chain termination with dideoxynucleotides. The desired DNA sequence is able to be determined by light emitted upon incorporation of the next complementary nucleotide by the fact that only one out of four of the possible A/T/C/G nucleotides are added and available at a time so that only one letter can be incorporated on the single stranded template (which is the sequence to be determined). A representative example can be found in the Article Pyrosequencing Sheds Light on DNA Sequencing, by Mostafa Ronaghi, Genome Research, 11:3-11(2001) which can be found at http://genome.cshlp.org/content/11/1/3.full.html#ref-list-1(as accessed on Dec. 23, 2013).

"Sequencing by Synthesis" means a technique used to determine the series of base pairs in DNA, also known as DNA sequencing. This sequencing method is based on reversible dye-terminators that enable the identification of single bases as they are introduced into DNA strands. Representative examples can be found at the websites: http://nxseq.bitesizebio.com/articles/sequencing-by-synthesis-explaining-the-illumina-sequencing-technology/ and http://www.iliumina.com/technology/sequencing_technology.ilmn (as accessed on Dec. 23, 2013).

"Sequencing by Oligonucleotide Ligation and Detection" means a way of generating hundreds of millions to billions of small sequence reads at one time. This is achieved by attaching small fragments of an unknown sequence to magnetic beads which then undergo immersion PCR. Representative examples can be found at the website: http://gtc.soe.ucse.edu/content/solid-technology-overview (as accessed on Dec. 23, 2013). And the sales brochure: See the Difference Discover the Quality Genome by Life Technologies Corporation (2010).

"Chain termination sequencing" means a method which requires a single-stranded DNA template, a DNA primer, aDNA polymerase, normal deoxynucleosidetriphosphates (dNTPs), and modified nucleotides (dideoxyNTPs) that terminate DNA strand elongation. These chain-terminating nucleotides lack a 3'—OH group required for the formation of a phosphodiester bond between two nucleotides, causing DNA polymerase to cease extension of DNA when a ddNTP is incorporated. The ddNTPs may be radioactively or fluorescently labelled for detection in automated sequencing machines. In some cases Chain termination sequencing may involve the synthesis of new strands of DNA complementary to a single-stranded template (step I). The template DNA is supplied with a mixture of all four deoxynucleotides, four dideoxynucleotides—each labeled with a different color fluorescent tag, and DNA polymerase (step II). As all four deoxynucleotides are present, chain elongation proceeds until, by chance, DNA polymerase inserts a dideoxynucleotide. The result is a new set of DNA chains all of different lengths (step III). The fragments are then separated by size using gel electrophoresis (step IV). As each labeled DNA fragment passes a detector at the bottom of the gel, the color is recorded. The DNA sequence is then reconstructed from the pattern of colors representing each nucleotide sequence (step V).

"Digital polymerase chain reaction" or (digital PCR, DigitalPCR, dPCR, or dePCR) means a refinement of conventional polymerase chain reaction methods that can be used to directly quantify and clonally amplify nucleic acids including DNA, cDNA or RNA. The key difference between dPCR and traditional PCR lies in the method of measuring nucleic acids amounts, with the former being a more precise method than PCR. PCR carries out one reaction per single sample. dPCR also carries out a single reaction within a sample, however the sample is separated into a large number of partitions and the reaction is carried out in each partition individually. This separation allows a more reliable collection and sensitive measurement of nucleic acid amounts. Representative examples are described in U.S. Pat. No. 6,143,496 and in the scientific article Digital PCR, by B. Vogelstein et al., Proc. Natl. Acad. Sci. USA, Genetics, Vol. 96, pp. 9236-9241, August (1999).

"Denaturing Gradient Gel Electrophoresis (DGGE)" means a form of electrophoresis which uses a chemical gradient to denature the sample as it moves across an acrylamide gel. DGGE can be applied to nucleic acids such as DNA and RNA, thus allowing the user to assess the number of different DNA/RNA sequences present in a sample. Representative example can be found in the Scientific Article: Profiling of Complex Microbial Populations by Denaturing Gradient Gel Electrophoresis Analysis of Polymerase Chain Reaction-Amplified Genes Coding for 16S rRNA, by G. Muyzer et al., Applied and Environmental Microbiology, Vol. 59, No. 3, pp. 695-700, March (1993).

"Defect" means an unwanted attribute of an item associated with a papermaking process. It includes but is not limited to one or more plugs on a felt, and such attributes of paper sheet as holes, discoloration, streaks, spots, translucent spots, and any combination thereof.

"Felt" means a belt made of interweaved wool or any other fiber used in a papermaking process which functions as a conveyer of materials wherein the interweaved fibers define a plurality of lumens through which water or other fluids may pass. Felts may also provide cushioning between press rolls and may also be a medium used to remove water from papermaking materials. Felts include but are not limited to bottom felts, bottom board felts, cylinder tissue wet felts, drier felts, endless felts, pickup felts, suction pickup felts, Harper top felts, and top felts.

"Paper Product or Paper Sheet" means any formed fibrous structure end product of a papermaking process traditionally, but not necessarily, comprising cellulose fibers.

Examples of such end products include but are not limited to facial tissue, bath tissue, table napkins, copy paper, printer paper, writing paper, notebook paper, newspaper, paper board, poster paper, bond paper, cardboard, and the like.

"Papermaking Process" means one or more processes for converting raw materials into paper products and which includes but is not limited one or more of such steps as pulping, digesting, refining, drying, calandering, pressing, crepeing, dewatering, and bleaching.

"PCR Analysis" means polymerase chain reaction analysis.

"Plug" means a solid, semisolid, viscous, and/or other deposit of material positioned within the lumens of a felt. Plugs may inhibit the flow of material through the lumens, and/or may impair any other functionality of a felt.

"Primer" means a composition of matter, typically a short strand of nucleotides, known to be complementary to specific sections of DNA and serve as a starting point for synthesis of a nucleotide chain complementary to DNA adjacent to the specific section of DNA.

"Probe" means a composition of matter constructed and arranged to bind to a targeted section of DNA and which can be readily detected when so bound and thereby be used to indicate the presence or absence of the targeted section of DNA.

"qPCR Analysis" means quantitative and/or qualitative polymerase chain reaction analysis.

"Microorganisms" means any organism small enough to insinuate itself within, adjacent to, on top of, or attached to equipment used in a papermaking process, it includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye, it includes but is not limited to any organism whose presence, in some way impairs the papermaking process such as forming plugs within felts and/or causing defects within paper sheets.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In at least one embodiment a highly sensitive and rapid detection method is provided for microorganisms located in paper sheets and machine felts. The method includes analysis of DNA present in samples extracts. The samples themselves are fragments of a felt or a sheet of paper. These samples are highly desiccated and contain little or no live samples of the contaminating microorganisms. Some prior art methods of utilizing DNA analysis include WO 2005/042082which describes an in situ method utilizing probes to determine the presence or absence of a microorganism. In situ methods however are not applicable to paper sheets or felts as they are dried out when sampled. Also the in situ method involves applying the probes during cell division of the microorganisms which is not possible on paper sheets or felts with little or no more living organisms on them. In at least one embodiment the DNA based analysis involves the use of probes.

In at least one embodiment the DNA based analysis involves the use of PCR primers to detect the presence or absence of microorganisms. U.S. Pat. No. 5,928,875 describes the use of PCR primers to detect the presence or absence of spore forming bacteria. In at least one embodiment the primer is targeted towards a part of a DNA strand which is highly conserved among a group of organisms. As a result, detecting the presence of that particular part of DNA is definitive proof of the presence a specific organism. PCR analysis is of particular use in analyzing felts and paper sheets due to the difficultly of correctly identifying its contaminating microorganisms because they lack viable organisms for traditional plating methods or ATP measurements. In at least one embodiment the PCR analysis involves utilizing one or more of the methods described in the Article Primer Directed Enzymatic Amplification of DNA with a Thermostable DNA Polymerase, by Randall Saiki et al., *Science*, Volume 239, pp. 487-491 (1988). In at least one embodiment the PCR analysis involves utilizing one or more of the methods described in the Article Specific Synthesis of DNA in Vitro via a Polymerase-Catalyzed Chain Reaction, by Kary Mullis et al., *Methods In Enzymology*, Volume 155, pp. 335-350(1987).

In at least one embodiment the PCR analysis is a qPCR analysis as described in Trade Brochure qPCR guide, prefaced by Jo Vandesompele, (as downloaded from website http://www.eurogentec.com/file-browser.html on Jan. 19, 2012). In at least one embodiment the method is a quantitative qPCR analysis. In at least one embodiment the method is a qualitative qPCR analysis.

As illustrated in FIG. 1, in at least one embodiment, the polymerase chain reaction (PCR) is a method for targeting sequences of nucleic acid (DNA or RNA) and increasing the copy number of the target sequence to obtain useful quantities of nucleic acid for down-stream analysis This method can be applied to the detection of microorganisms in a variety of samples that include, but are not limited to, machine felts, sheet defects, machine deposits, etc. As illustrated in at least one embodiment, once DNA is extracted from the sample, using any of the DNA extraction kits available commercially, it can be analyzed in real-time using a PCR approach such as a Quantitative PCR approach. Quantitative PCR utilizes the same methodology as PCR, but it includes a real-time quantitative component. In this technique, primers are used to target a DNA sequence of interest based on the identity of the organism or function of a specific gene. Some form of detection such as fluorescence may be used to detect the resulting DNA or 'DNA amplicon'. The change in fluorescence is directly proportional to the change in the quantity of target DNA. The number of cycles required to reach the pre-determined fluorescence threshold is compared to a standard that corresponds to the specific DNA target. A standard is typically the target gene that is pure and of known quantity at concentrations that span several logs. The number of copies of target DNA present in the sample is calculated using the standard curve. The copy number per sample is then used to determine the number of cells per sample.

In at least one embodiment a primer set is used which targets DNA sequences from bacteria using a conservative approach to quantify total bacteria. In at least one embodiment a primer set is used which targets primary biofilm-forming bacteria, including *Meiothermus*, *Pseudoxanthomonas*, and *Deinococcus*. In at least one embodiment a primer set is used to target an adaptive biofilm-former which belongs to the Sphingomonadacea family of bacteria. In at least one embodiment the adaptive biofilm-former exhibited higher tolerance to oxidant-based biocontrol programs compared to other biofilm and planktonic microorganisms. In at least one embodiment the primer is used to distinguish between fungal and bacterial infestations.

Machine felts commonly pass in and out of shower streams and liquid basins containing various microorganisms from which live samples can be easily obtained. However the dynamic state of the felt (rapidly changing from wet to dry conditions, the rapid passing through of air and liquids, and the soft substrate which bends, flexes, and rolls) often means that the population of organisms inhabiting the felt will differ from those present within the shower streams and liquid basin it contacts. As a result a typical analysis of the shower streams and liquid basins will not correctly identify what microorganisms are present within the felt. A PCR analysis of a felt sample which takes into account the sorts of organisms which are known to be able to inhabit felts however allows for a truly accurate analysis of felt contaminations.

In at least one embodiment the DNA based analysis of the sample involves discounting the possibility of the presence of microorganisms known to not inhabit machine felts and/or end product paper sheets. In at least one embodiment the method involves limiting the primers used to those associated with organisms known to inhabit machine felts and/or end product paper sheets.

In at least one embodiment the method involves distinguishing between DNA at the biological kingdom level. Biological life can be categorized according to five kingdoms: Monera, Protist, Plant, Animal, and Fungus. These organisms have hugely differing DNA and a protocol which focuses on identifying the organism's DNA at the kingdom level is vastly simpler than more specific determinations. Because with felts, the organisms from different kingdoms are often best treated differently, such a simple form of identification can be used to accurately identify the specific regimen best targeted to the particular contaminant.

In at least one embodiment more than one primer is used to identify organisms that have more than one uniquely recognizable nucleotide sequence. In at least one embodiment the PCR analysis is used to detect genome sequences associated with enzymes unique to or nearly unique to specific organisms.

In at least one embodiment the method involves detecting a defect and then utilizing the PCR analysis to properly associate the source of the defect. In at least one embodiment the method determines if the defect is totally biologically based, totally non-biologically chemical based, or resulting from a combination of non-biologically chemical, mechanical, and biologically based sources.

In at least one embodiment the defect is one or more plugs on a felt. In at least one embodiment the defect is a paper sheet having at least one or more of: a hole, a hole with a discolored halo around at least a portion of it, a streak of discoloration, a spot, a translucent spot, and any combination thereof.

In at least one embodiment a threshold level is methodology used to discount false positives. Sometimes PCR analysis detects traces of organisms that while present are not causes of a particular defect. In at least one embodiment the method involves discounting the presence of any organism detected at a concentration lower than a pre-determined level known for one or more particular organisms. In at least one embodiment the method involves discounting the presence of any organism detected at level lower than $10^4$ cells per gram (of the defect). In at least one embodiment the method involves discounting the presence of any organism detected at level lower than $10^4$ cells per ml.

In at least one embodiment the results of the analysis are used to augment the biocontrol program by determining how much, what kind, and how often, one or more biocidal compositions are added to one or more locations within a papermaking system. In at least one embodiment any and all of the above and below embodiments are applied to a process water system or industrial system other than a papermaking process.

In at least one embodiment the method is able to detect microorganisms that would not otherwise be detected by prior art methods. For example in cases where foulant is caused by an infestation of anaerobic or sulfate reducing organisms, methods such as ORP detection would not correctly identify the foulant source as biological and would therefore incorrectly suggest applying an chemical not an anti-bilogical approach. Utilizing the DNA approach would however always correctly indicate a biological infestation because all life contains DNA.

In at least one embodiment a method is used for assessing microbial diversity. This can include problematic microorganisms found in machine deposits, sheet defects, finished products, felts, etc. The method is based on analysis of nucleic acids in sample extracts. More specifically, it utilizes PCR such as but not limited to qPCR for the detection of total organisms such as bacteria; *Sphingomonas.* species; *Erythrobacter* species; *Pseudomonas* species; *Burkholderia* species; *Haliscomenobacter* species; *Saprospira.* species; *Schlegelella.* species; *Leptothrix.* species; *Sphaerotilus* natans; *Bacillus* species; *Anoxybacillus.* species; members of the *Cytophaga-Flavobacterium-Bacteroides* phylum; green nonsulfur bacteria, including *Herpetosiphon*, members of the *Deinococcus-Thermus* phylum, including *Meiothermus* species; catalase-producing bacteria, amylase-producing bacteria, urease-producing bacteria, fungi, etc. These techniques utilize primers and standards pairs that allow for detection and quantification of target organisms based on conserved sequences. The primers target regions in the microbial genome that are highly conserved through evolution, while primers for specific phyla or genera target more variable regions of the genome.

Being able to accurately quantify an organism of interest present in a sample makes it possible to express that organism as a percentage of the total bacterial load in the sample. Given the large number of organisms that can be detected, a snapshot of the diversity of the microbial population in sample can be determined (FIG. 1). This snapshot is called the diversity index. The diversity index can also be expressed quantitatively as the relative abundance of several target organisms. The diversity index for any part of a process can be measured at times when machines or processes are running well, thus creating a baseline. The diversity index measured at times of poor machine or process performance can then be compared to the baseline to look for fluctuations in microbial populations and to determine which bacterial groups are responsible for problems in the process. The diversity index can also be quantified for ease of comparison using the Shannon diversity index calculation to compare monitoring data among sample locations or relative to a baseline. Treatment strategies and feed points can then be altered accordingly to combat the problem.

A diversity index based on quantification of DNA measures the presence and diversity of organisms in a process, independent of their viability. Ribonucleic acid (RNA), specifically messenger RNA (mRNA), is a molecule that is produced only by living organisms, and has properties such that, depending on the target, are unique to a specific phylum or genera of bacteria. By amplifying mRNA sequences that are unique to the organisms listed above it becomes possible to determine which bacteria are present in their viable form. Accurate detection of viable organisms can then be used as a tool for assessing the efficacy of treatment strategies of process waters. This can be accomplished by comparison of the diversity index to the viability index.

This method would quantify the amount and type of viable bacteria present in process samples. The quantitative (real time) polymerase chain reaction method can be applied to detect messenger ribosomal nucleic acids (mRNA). mRNA is transcribed DNA that is sent to the ribosome to serve as a blueprint for protein synthesis in a process known as translation. mRNA is produced only by living cells. RNA from living cells can be isolated with the use of commercially available kits. Detection of mRNA requires an extra step in the quantitative polymerase chain reaction. Reverse transcriptase is added to the reaction cocktail to transcribe mRNA into its complementary DNA (cDNA). Two sets of primers are required for this experiment. The first targets specific mRNA, while the second is used to amplify the resulting cDNA produced by the reverse transcriptase reaction.

EXAMPLES

The foregoing may be better understood by reference to the following examples, which are presented for purposes of illustration and are not intended to limit the scope of the invention.

A coated free sheet mill experienced persistent deposition in one of the machine headboxes, which was believed to be the cause of defects in the final product. Microorganisms were assumed to be the underlying cause of the problem. However, traditional monitoring techniques (e.g. standard plate counts and ATP levels) did not indicate elevated levels of microbial activity.

Deposit samples from the headbox were analyzed over the course of several months using qPCR techniques. Initial qPCR results from the analysis of headbox deposits exhibited high levels of microbial loading, as well as elevated densities of primary and adaptive biofilm-formers (FIG. 1). The treatment strategy was augmented with the addition of biocides to both the pulper and the broke silo. The feed rate of the oxidant-based biocontrol program was also increased. Analysis of deposits collected one month later detected little change in the total bacterial load of the headbox deposits (FIG. 1A). The number of primary biofilm-formers decreased one-log, while the density of adaptive biofilm-formers decreased four-logs (FIG. 1B and 1C). The amount of headbox deposits and frequency of sheet defects continued to remain unchanged. Traditional plating and ATP analysis of the stock and process water system indicated little biological activity. The ATP and plate count values were averaging less than 100RLU and 100colony-forming units per gram (CFU/g), respectively.

The treatment strategy was further optimized through the addition of unstabilized chlorine and biocides to the broke silo and the pulper. After implementation of the last set of changes, additional samples were collected and analyzed. The total bacterial load of the deposit showed a decrease of nearly one-log (FIG. 1A). The final set of deposit samples showed a decrease of nearly two-logs in the density of primary biofilm-formers (FIG. 1B). Adaptive biofilm-formers remained at near-background levels (FIG. 1C). Again, despite improved control of the microbial population, the defect frequency, the nature of the defects, and headbox deposition remained unchanged.

Sheet defects from this mill were analyzed using the same qPCR-based approach. It is impossible to determine bacterial content in defects using traditional plating and ATP methods because many of the bacteria that may have been present in the defect are killed by the high temperatures of the dryer section. Chemical analysis does not provide a definitive answer about bacteria present in the sheet as it relies on ninhydrin staining.

Figure 2:
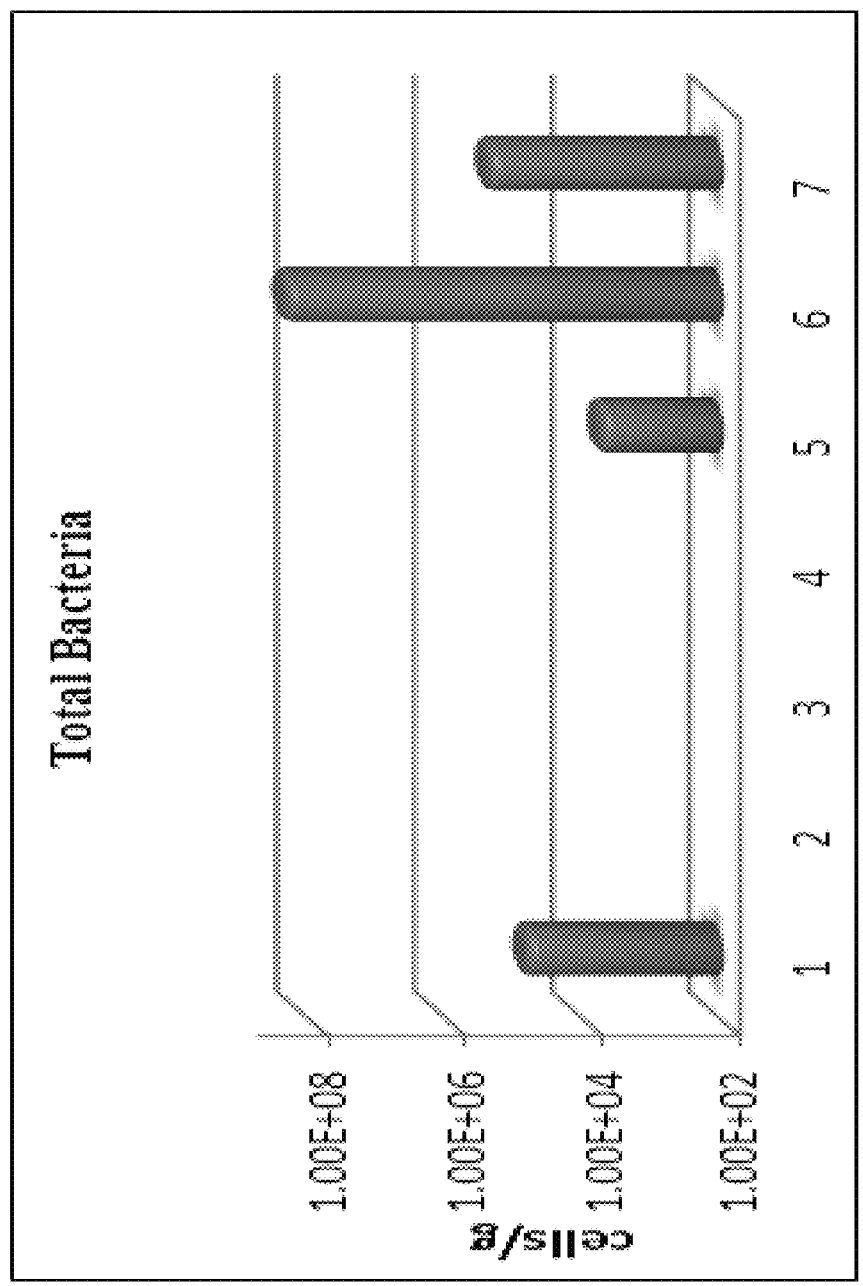

This approach is non-specific and prone to false positive and false negative results. DNA analysis of holes and sheet defects from this mill detected very low bacterial density (FIG. 2, Samples 1-5). Primary and adaptive biofilm-formers were not detected in the sheet defects analyzed from this mill. Therefore, bacterial slime was not likely contributing to defects and quality issues at this mill. In comparison, a mill suffering from significant biological deposition had defects containing much higher microbial loading (FIG. 2, Sample 6). Furthermore, similar bacterial species were identified in the deposits and defects. Ninhydrin staining of these defects did result in a positive reaction indicating the presence of microorganisms. In another case, bacteria were detected in sheet defects at levels just above the minimum density required to be considered a biological defect. However, the ninhydrin reaction was negative indicating the defect did not contain microorganisms (FIG. 2, Sample 7). Quantitative qPCR examination of headbox deposits demonstrated reductions in both primary and adaptive biofilm-formers following each modification to the treatment strategy. The fact that there was a drastic decrease in these target organisms and no decrease in the amount of deposition or defect frequency, indicates that bacteria are likely not responsible for defect problems in this machine system. Primary biofilm-formers colonize machine surfaces and create a favorable environment for attachment and proliferation of other organism types. Without the presence of these organisms, bacteria may attach to machine surfaces following the deposition of chemical debris that can serve as a good growth medium. It is likely that chemical additives and fiber were depositing inside the headbox, resulting in a microenvironment suitable for microbial colonization. Since the analysis of sheet defects revealed negligent microbial presence, microorganisms were ruled out as the primary source of deposition in the headbox and adverse effects on product quality. Efforts to improve machine performance were focused away from biocontrol and toward better mechanical control of the system allowing for improved operational conditions and product quality.

A coated free sheet mill utilized a competitive oxidant-based biocontrol program for several years. Control of microbial growth was perceived as adequate; however, there was an opportunity to further reduce sheet breaks for improved process efficiency. The program was implemented and optimized in several phases. Bacterial density throughout the process remained low and a reduction in sheet breaks was documented. The average number of breaks per day decreased from an average of 1.2 breaks per day to 0.42 breaks per day.

Figure 3:
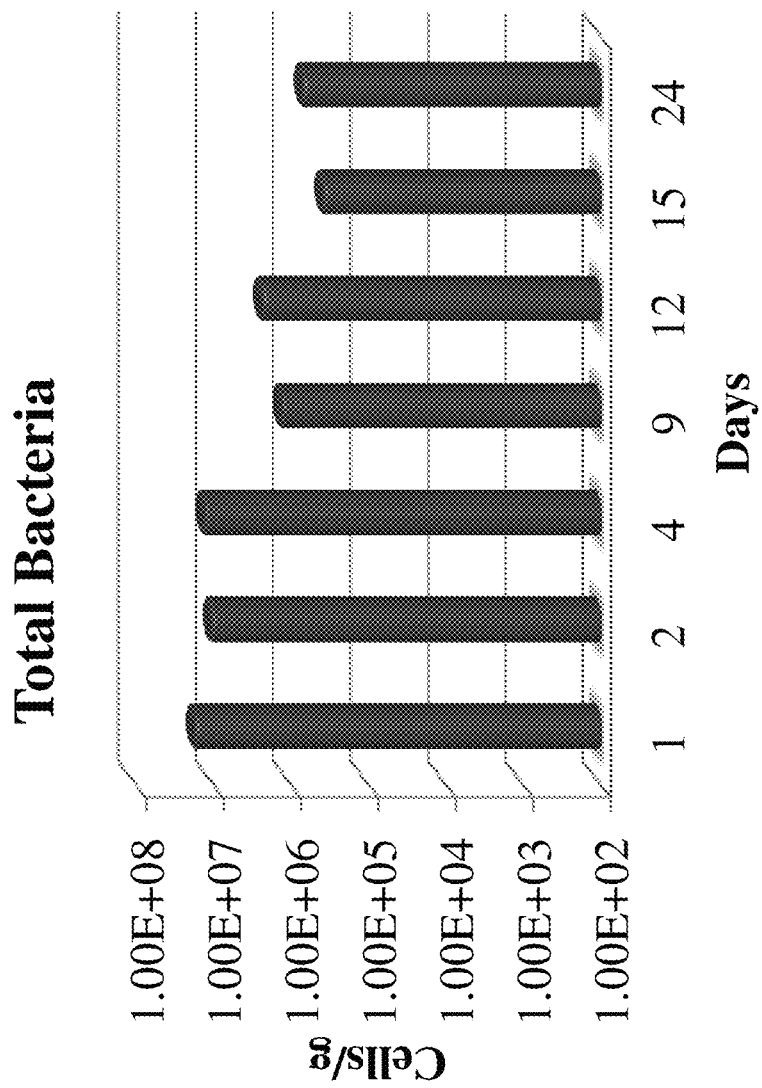

Approximately two-years after the implementation of the optimized program, it was observed that process conditions had become more variable and increasing concentrations of biocontrol products were required to maintain the same level of control. A system survey using traditional monitoring tools such as plate counts and ATP measurements, indicated that bacterial density in the process water system remained low and no or little increase was observed in the headbox and broke system. However, the mill was suffering a severe outbreak of holes and defects. While traditional monitoring techniques indicated no change in the performance of the biocontrol program, the on-line activity monitor detected increasing microbial activity (FIG. 3).

Quantitative qPCR analysis of the machine deposits and sheet defects all confirmed the presence of primary and adaptive biofilm-formers. The density of total bacteria in the defects was approximately $1.8 \times 10^7$ cells per gram (FIG. 3). This evidence indicates the role of microorganisms in the defect and quality issues. The machine underwent a caustic boilout after which, the online activity monitor demonstrated a reduction in microbial activity and a more stable ORP value indicating improved program performance and resilience. The amount of microorganisms in sheet defects decreased from $10^7$ to $10^5$ cells/g following the boilout (FIG. 3). This confirms that qPCR can detect microbial contribution to sheet defects which cannot be detected using traditional techniques. In addition, qPCR can be used to assess the efficacy of the biocontrol program on the final product.

Figure 4:
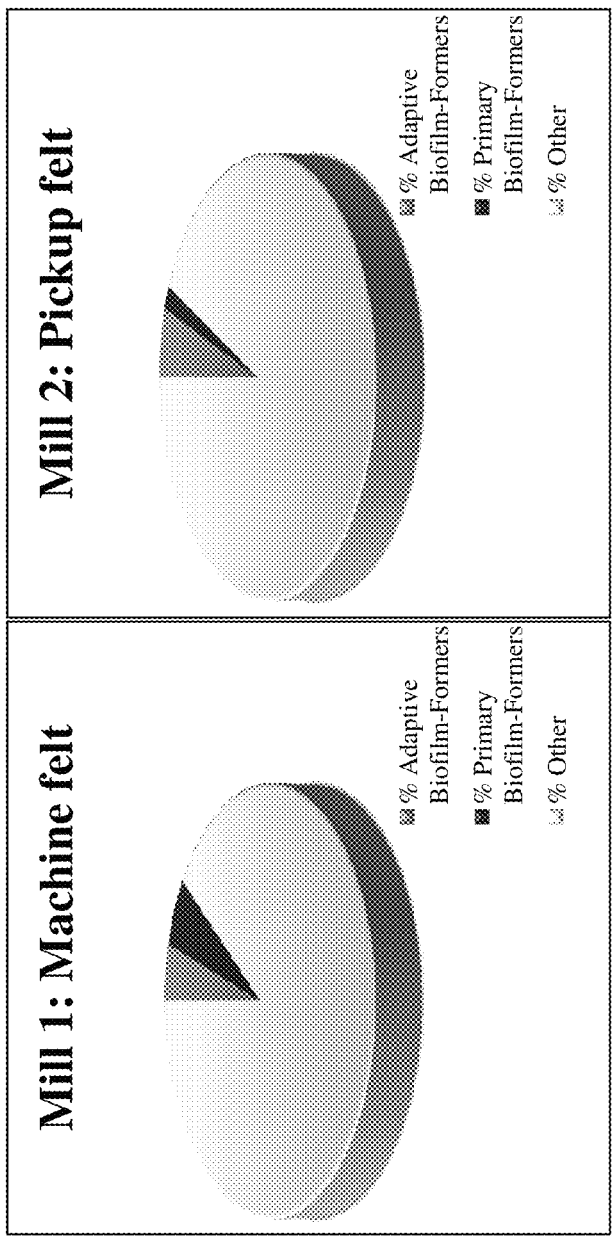
FIG. 4 illustrates pie charts denoting microbial diversity varied in DNA samples collected from machine felts from two different paper mills.

Felt samples from two paper mills that were experiencing performance issues, which manifested themselves as on-machine deposits and sheet defects, were analyzed using qPCR. Each sample was tested for the presence of microorganisms. Once it was determined that each sample contained high amounts of bacteria, the samples were then analyzed for the presence of adaptive and primary biofilm-formers, which included *Sphingomonadaceae*. fm., *Meiothermus, Geothermus*, and *Pseudoxanthomonas*. which have been known to contribute to problems with machine efficiency and product quality. Both mills contained normal levels of adaptive biofilm-formers, however, Mill 1 had twice as many primary biofilm formers as Mill 2 (FIG. 4). The level of adaptive biofilm formers was determined to be normal as its levels were in the range that indicated it is likely not contributing to the problem. The level of primary biofilm-formers at Mill 2 was at a near-background level. High levels of primary biofilm-formers at Mill 2 suggested biofilm formation in felts which leads to felt plugging and reduced water removal from the sheet. The presence of biofilm on the felts can lead to increased deposition of other matter which can then redeposit onto the sheet. Elevated levels of primary biofilm-formers at Mill 1 suggested that additional analysis of other parts of the process such as shower water, additives, storage chests, etc. were needed to determine where these organisms were originating.

The result of these examples demonstrates that conventional plating techniques and oxidant residuals may indicate adequate biocide dosing and control of microbial growth, while deposition, defects and breaks remain prevalent. Utilizing PCR and qPCR methods provide more accurate information regarding microbial growth and biofilm formation in industrial water systems. These strategies allow for rapid analysis of the contribution of microorganisms to deposit formation and can be used to rapidly determine whether or not deposits containing microorganisms are contributing to defects.

Quantitative qPCR techniques allow for rapid analysis of sheet defects to determine the contribution of microorganisms to quality issues. This new approach has been demonstrated to allow for a more proactive diagnosis of problems leading to improved machine efficiency and product quality.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or some of the various embodiments described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of identifying an organism infestation in a papermaking process, the method comprising the steps of:
noting a defect on an item associated with a papermaking process,
conducting at least one DNA analysis on at least one sample taken from the item, the DNA analysis targeted towards nucleotide sequences associated with types of organisms known to inhabit a type of item on which the defect is noted,
if a positive result is indicated, determining if a measured concentration of organisms of the type targeted in the at least one DNA analysis exceeds a first pre-determined threshold,
if the measured concentration exceeds the first pre-determined threshold, conducting at least one additional DNA analysis to determine specific organisms that are present in the sample, wherein the specific organisms are of the type targeted in the at least one DNA analysis, and
if the measured concentration of a specific organism determined to be present exceeds a second pre-determined threshold, determining that the defect is at least in part due to an infestation of that organism.

2. The method of claim 1 in which the item is a felt and the defect is one or more plugs in the felt.

3. The method of claim 1 in which the item is a paper sheet produced by the papermaking process and the defect is one or more holes, discoloration, streaks, spots, translucent spots, and any combination thereof on the paper sheet.

4. The method of claim 1 further comprising the step of recording the specific organism determined to be present into a format which can be stored and/or transmitted.

5. The method of claim 1 further comprising the step of conducting a biocidal program associated with remedying the specific organism determined to be present.

6. The method of claim 1 in which the DNA Analysis is one selected from the list consisting of qPCR, PCR, digital PCR, ion semiconductor sequencing, pyrosequencing, sequencing by synthesis, sequencing by litigation, chain terminating sequencing, and any combination thereof.

7. The method of claim 1 in which the second pre-determined threshold is $10^4$ cells per ml of the defect or $10^4$ cells per gram of the defect.

8. The method of claim 1 in which the item is so desiccated that there are little or no living organisms on the item that may have caused the defect.

9. The method of claim 1 in which the conditions of the item differ so much from the fluids the item encounters during the papermaking process that the organisms which inhabit the item differ from those in the fluids and determining the inhabitants of the fluids will produce an incorrect identification of the organisms on the item causing the defect.

10. The method of claim 1 further comprising the step of applying sufficient kinds of primers to samples of the item such that the presence of any organisms above the first pre-determined threshold can be determined.

11. The method of claim 10 further comprising the step of identifying the defect as being non-biologically based if the DNA analysis does not indicate that any organisms exceed the first pre-determined threshold.

12. The method of claim 11 further comprising the step of applying a remedy for non-biological chemical contamination to the papermaking process.

13. The method of claim 1 in which the DNA analysis determines the quantity of organisms infesting the sample.

14. The method of claim 1 in which the item has passed through a heat or dryer section of the papermaking process before the defect is noted and therefore the organisms which caused the defect have been killed.

* * * * *